(12) United States Patent  (10) Patent No.: US 8,657,851 B2
Aufaure et al.  (45) Date of Patent: Feb. 25, 2014

(54) SURGICAL TWEEZERS

(75) Inventors: Jean-Luc Aufaure, Souvigny (FR); Antoine Sempe, Les Moulineaux (FR)

(73) Assignee: Moria SA, Antony (FR)

( * ) Notice: Subject to any disclaimer, the term of this patent is extended or adjusted under 35 U.S.C. 154(b) by 1252 days.

(21) Appl. No.: 12/469,992

(22) Filed: May 21, 2009

(65) Prior Publication Data

US 2010/0298865 A1  Nov. 25, 2010

(51) Int. Cl.
*A61B 17/50* (2006.01)

(52) U.S. Cl.
USPC ............ 606/210; 606/51; 606/52; 606/205; 433/4; 81/3.6; 81/354

(58) Field of Classification Search
USPC ............ 606/205, 210, 51–52; 433/4; 81/3.6, 81/354
See application file for complete search history.

(56) References Cited

U.S. PATENT DOCUMENTS

| | | | |
|---|---|---|---|
| 4,318,313 A * | 3/1982 | Tartaglia | 294/99.2 |
| 4,938,214 A * | 7/1990 | Specht et al. | 606/174 |
| 5,019,091 A * | 5/1991 | Porat et al. | 606/205 |
| 5,108,392 A * | 4/1992 | Spingler | 606/51 |
| 2009/0267372 A1* | 10/2009 | Chen | 294/99.2 |

* cited by examiner

*Primary Examiner* — Victor Nguyen
*Assistant Examiner* — Kevin Everage
(74) *Attorney, Agent, or Firm* — Muncy, Geissler, Olds & Lowe, P.C.

(57) ABSTRACT

The invention provides tweezers for microsurgery, in particular opthalmological surgery, the tweezers comprising a one-piece working part (1) of U-shape, with the free ends (2a, 3a) of each branch (2, 3) being shaped into a point, the part being derived from a flat blank of thickness (e) constituting the dimension perpendicular to the plane (P) in which the branches (2, 3) move, and elements for manipulating the working part together forming a handle for gripping the tweezers, wherein each element is in the form of an elongate body (4, 5) presenting a convex outside surface (4a, 5a) and a substantially plane surface (4b, 5b) having a longitudinal groove (6, 7) hollowed out therein to house one of the branches (2, 3) of the working part (1), the end of each handle element facing towards the points being provided with centering means (8a, 8b, 9a, 9b) co-operating with a complementary centering member of the corresponding end of the other element.

7 Claims, 3 Drawing Sheets

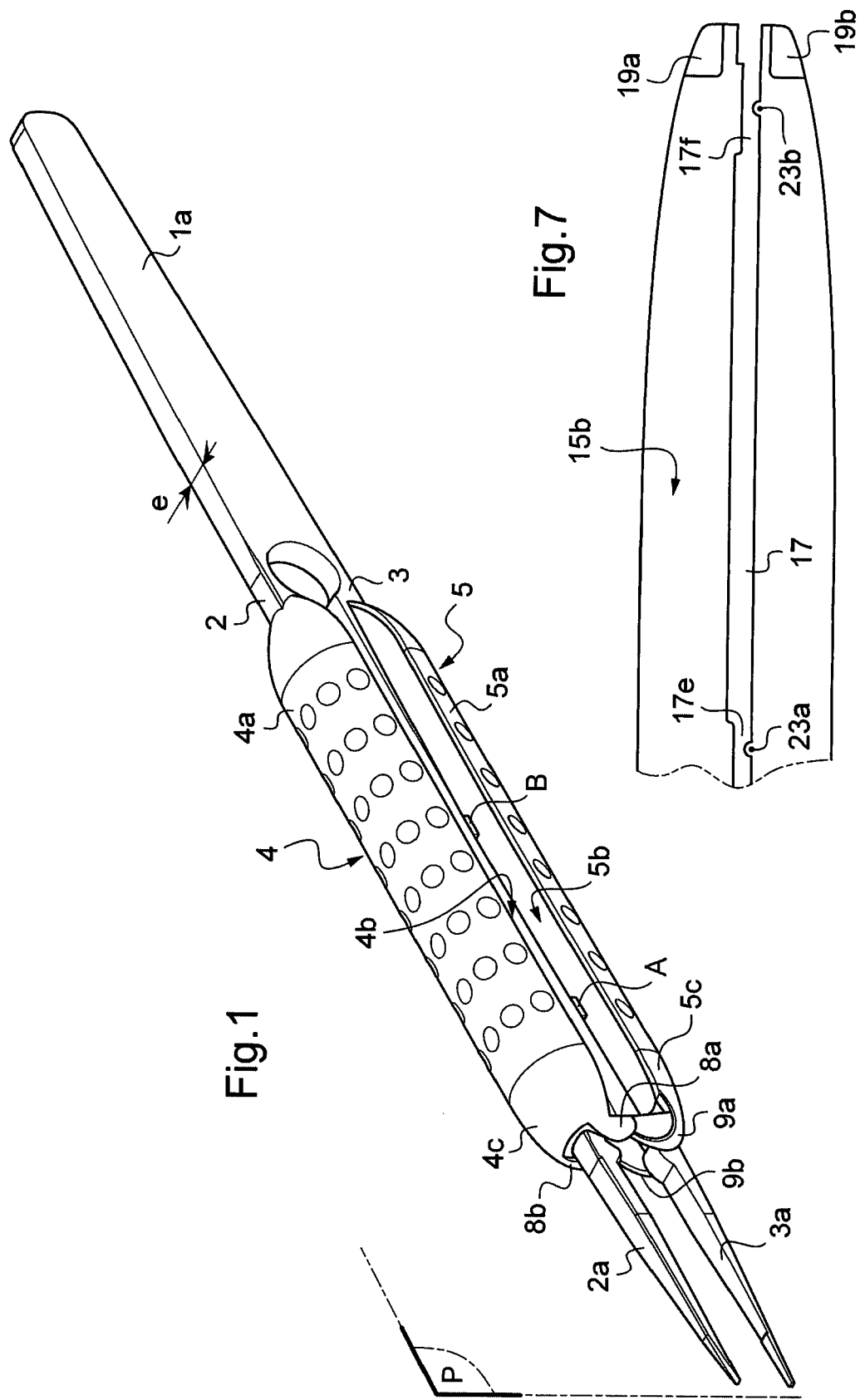

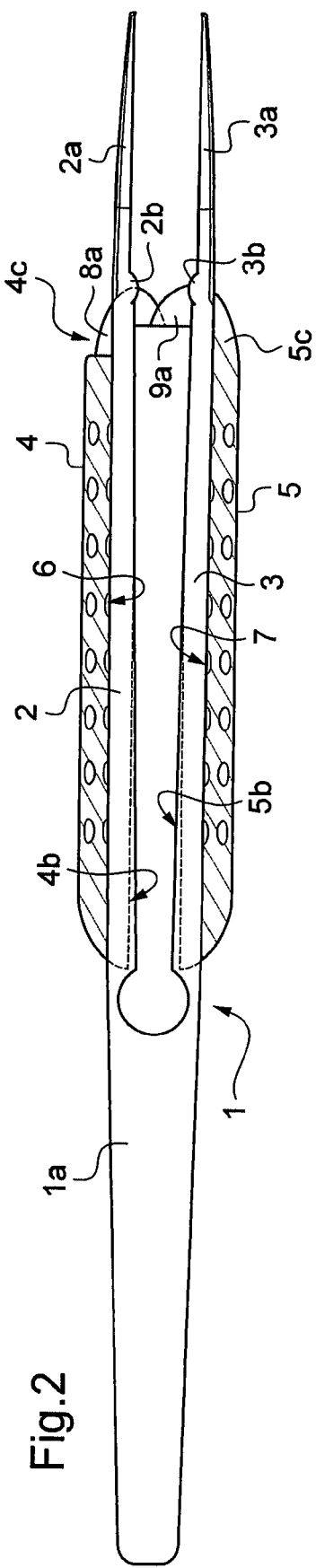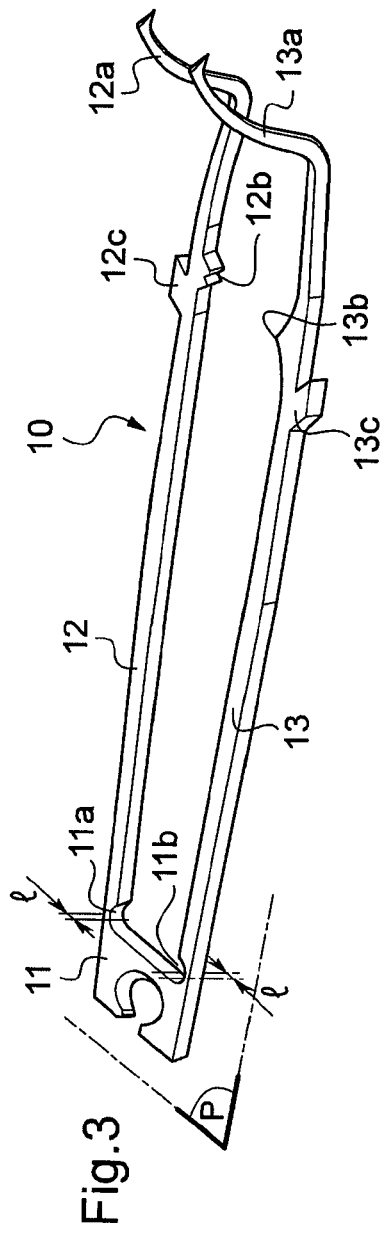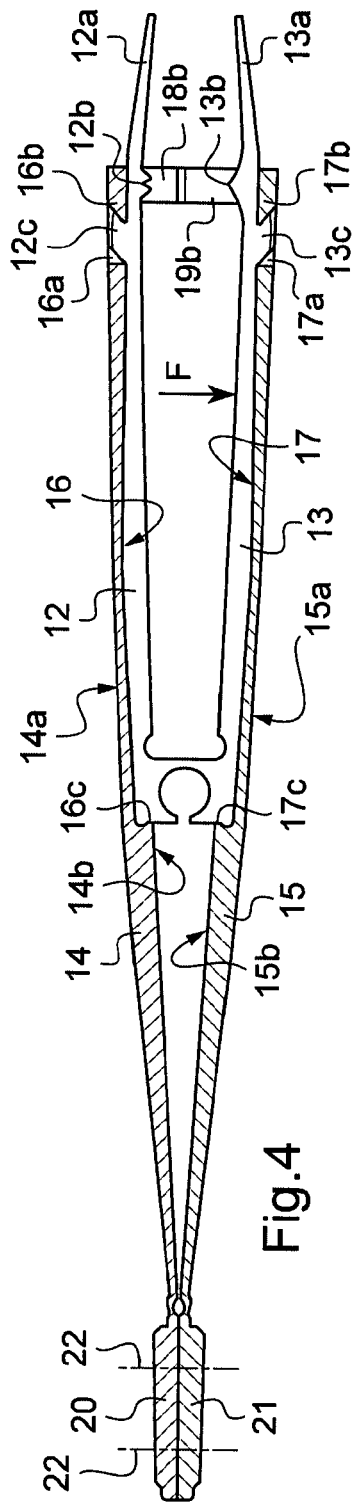

SURGICAL TWEEZERS

The present invention relates to surgical tweezers, and more particularly to surgical tweezers for opthalmological surgery.

BACKGROUND OF THE INVENTION

Surgery of the eye requires instruments that are small and fine to act through openings of small size and on organs or tissue that are likewise of small size.

Certain tweezers of this type are made from two metal blades that are hinged together in their middle portions or close to their active ends. The precision of the active ends of tweezers of this type depends on the care with which they are fabricated, and in particular on the slack that exists in the hinge. Furthermore, in use, this slack increases and precision decreases.

There also exist tweezers that are made from flat blades that are curved perpendicularly to their thickness and that are united at their ends remote from their active ends. The stiffness of the arms formed by the blades is generally not satisfactory, and the practitioner does not have sufficient feel when handling the tweezers.

Reducing the costs of fabricating this type of equipment is a constant preoccupation for manufacturers, particularly since single use is preferred over multiple use with sterilization after each use. Microsurgery tweezers have thus appeared on the market that are made of plastics material, but that do not give satisfaction insofar as the active portions of the tweezers are lacking in fineness and hardness. Proposals have therefore been made for composite tweezers in which the active portions are made of two metal points with a single piece of plastics material molded thereover to act both as the grip or handle portion of the tweezers and to move the points apart from each other resiliently. The greater or smaller flexibility of such tweezers is determined by the plastics portion, and is not stable over time. The plastics material is subjected to severe treatments by the sterilization procedures to which the tweezers are subjected, thereby accelerating aging thereof and causing its qualities to degrade quickly.

Another drawback of that type of equipment is that plastics material does not make it possible to guarantee that the active points of the tweezers are properly aligned when they move towards each other. It is therefore necessary to incorporate special centering means in the metal portions of the tweezers such as a stud being engaged in a hole, each formed in a respective one of the branches of the tweezers.

Finally, there exist tweezers in which the arms comprise the two branches of a U-shaped pin cut out from a metal sheet, each of the arms then being fitted with a handle against which the fingers of the surgeon press. One of the advantages of such tweezers lies in the precision of manufacture that can be obtained at low cost. The working points or hook-shaped tips are themselves reworked so as to refine their ends, regardless of whether they are in line with the arms, i.e. in the plane of the metal sheet (points) or are curved out from said plane (hook-shaped tips), i.e. raised from the plane of the metal sheet. Nevertheless, it is found that it is still necessary, as with other prior art tweezers, to guide the points or hook-shaped tips so that they coincide exactly when the tweezers are closed.

In tweezers obtained by cutting out, there is not enough metal in each branch for that to be achieved.

The present invention seeks to propose tweezers in the form of a U-shaped metal pin obtained either by being cut out from metal sheet or by the metal injection molding (MIM) technique, the tweezers being fitted simply with means that enable their working points to coincide accurately when the surgeon handles the tweezers.

OBJECT OF THE INVENTION

The present invention thus provides tweezers for microsurgery, in particular opthalmological surgery, the tweezers comprising a one-piece working part of U-shape, with the free ends of each branch being shaped into a point, the part being derived from a flat blank of thickness constituting the dimension perpendicular to the plane in which the branches move, and elements for manipulating the working part together forming a handle for gripping the tweezers, wherein each element is in the form of an elongate body presenting a convex outside surface and a substantially plane surface having a longitudinal groove hollowed out therein to house one of the branches of the working part, the end of each handle element facing towards the points being provided with centering means co-operating with a complementary centering member of the corresponding end of the other element.

It has been found that distortion of the tweezers is due to the direction of the force applied thereto by the surgeon's fingers. This force need not necessarily lie exactly in the plane of movement of the branches of the U-shape, but may be inclined relative to said plane, thereby creating a transverse component in addition to the squeezing force, thereby leading to the plane of the working part being warped and thus to the points being offset sideways. The centering means of the invention serve to oppose this warping by taking up the transverse component of the squeezing force.

In a preferred embodiment of the invention, the centering means are constituted at least by fins provided on one of the bodies and projecting towards the other body beyond the plane surface having the groove so as to fit closely on either side of a complementary portion at the end of the other body during closure of the tweezers.

The fins in question advantageously diverge away from the plane surface while the complementary portion presents the shape of a wedge having two slopes that becomes progressively received between the fins during the closure movement of the tweezers.

According to a feature of the invention, each branch is provided, facing the other branch, with a projection constituting an abutment for stopping closure, said abutment being situated level with the above-mentioned centering means.

The two handle elements of the tweezers are of a length shorter than the total length of the working part. Each is then fitted on the corresponding branch by engaging the branch in the groove and by fastening by any means appropriate for the materials constituting the working part and the handle (laser welding if they are both made of metal, adhesive, snap-fastening, . . . ). Under such circumstances, the working part possesses a root portion of the branches that extends well beyond the rear ends (proximal ends) of the handle elements so as to assist in handling of the tweezers by the operator.

In a variant embodiment, the handle elements extend beyond said proximal end of the working part and are united via their ends that lie outside the working part.

According to an important characteristic of the invention, each branch of the working part extends from a root portion forming the base of the U-shape via a zone that is of controlled width. By controlling the width of this zone during fabrication, it is possible to adapt the stiffness of the tweezers, i.e. the extent to which they oppose the squeezing force.

Depending on the use made of the tweezers, their stiffness needs to be greater or smaller (in general greater for an operation that requires precision).

Mention is also made of a particular embodiment of the invention in which the handle elements are made of injected plastics material, wherein each element includes a groove having at least two zones that are of calibrated width and with a bottom that includes an opening for receiving an inclined connection tooth on the outside of a branch of the tweezers, the proximal end of the groove being suitable, in co-operation with the tooth, for preventing the handle element moving on the working part, while the end of said handle element is shaped as a flat tail substantially perpendicular to the plane of the working part in service, said tail being provided with pressure-operated snap-fastener means co-operating with complementary means provided on the tail of the other handle element.

According to another characteristic of the invention when made as above with separate handle elements of plastics material, at least one or the other of the fins or of the complementary portions includes portions in relief on at least one of its active faces such that on the first occasion the branches of the tweezers are moved towards each other, the portions in relief are flattened, at least in part, by plastic deformation.

This provision makes it possible to obtain excellent engagement between the points or the hooks of the tweezers, in spite of the dimensional uncertainties of parts made of plastics material.

Finally, in order to control interaction between the working part and the plastics handle, i.e. to ensure that the forces on each of them serve to ensure that the handle elements are held properly on the working part with stresses in balance so that no distortions are generated that might spoil the coincidence qualities, or lead to deterioration in coincidence qualities over time as a result of successive sterilizations, one of the flanks of each groove is provided with at least one portion in relief that is suitable for being deformed plastically by inserting the working part in the groove.

BRIEF DESCRIPTION OF THE DRAWINGS

Other characteristics and advantages of the invention appear on reading the following description of a few embodiments. Reference is made to the accompanying drawings, in which:

FIG. 1 is an outside view showing the distal end of a microsurgery tweezers in accordance with the invention;

FIG. 2 is a section view of the tweezers;

FIG. 3 is a perspective view of a working part in which the tweezers are spout- or hook-shaped;

FIG. 4 is a longitudinal section view of a second embodiment of the invention;

FIG. 7 is a detail view of a handle element made of plastics material for tweezers of the invention.

DETAILED DESCRIPTION OF THE INVENTION

Figure 5:
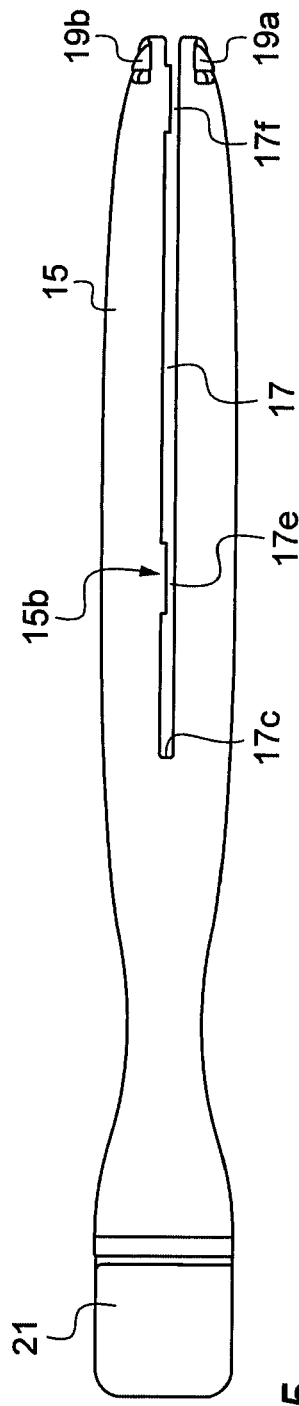
FIG. 5 is a plan view of a handle element for a FIG. 4 pair of tweezers.

FIGS. 1 and 2 show tweezers for opthalmological surgery that comprise a one-piece working part 1 that is U-shaped, being obtained by cutting a metal sheet with a wire (electro-erosion) or by any other technique such as precision electro-chemical machining (PECM). This part 1 thus has two branches 2 and 3, with the free ends 2a and 3a of each of the branches being shaped into a point, in particular by machining. The thickness e of the metal sheet (or more generally of a flat blank that might be a plate of synthetic material, either of the type comprising a polymer matrix filled with a reinforcing material, or of the composite type, or obtained by the metal injection molding (MIM) fabrication method) is constituted by the dimension perpendicular to the plane P in which the branches move.

The tweezers also have elements 4 and 5 for manipulating the working part 1, together forming a handle for gripping the tweezers.

Each element 4, 5 is in the form of an elongate body presenting an outside surface 4a, 5a that is convex and a surface 4b, 5b that is substantially plane and that has a longitudinal groove 6, 7 hollowed out therein to receive a branch 2, 3 of the working part 1. The convex surface constitutes the grip surface of the tweezers and is provided with any texturing or coating that is appropriate for improving comfort and quality of grip.

The end 4c, 5c of each handle element that faces towards the point 2a, 3a is provided with a centering member that co-operates with a complementary centering member for the corresponding end of the other element. In FIGS. 1 and 2, these centering means are constituted by at least two fins 8a, 8b provided on the body 4, and 9a, 9b provided on the body 5, the fins projecting from the grooved plane surface 4a, 5a of the corresponding body towards the other body. The fins 8a, 8b of the body 4 fit closely around the fins 9a, 9b carried by the other body 5. Thus, they slide with very small clearance and they overlap in part even at rest, as shown in FIGS. 1 and 2, thereby preventing any warping of the tweezers in spite of the existence of a transverse component in the force exerted on the tweezers in order to close them, thus keeping the points in alignment until they make contact. In a variant embodiment, the outside surfaces of the fins 9a, 9b may converge towards each other going towards the body 4, while the inside surfaces of the fins 8a, 8b diverge away from each other going towards the body 5; the cam effect that results from this configuration enables the points to be realigned progressively as the tweezers are squeezed.

It should be observed that each branch of the tweezers presents a projection 2b, 3b facing the other branch and constituting an abutment that limits the extent to which the two branches can be moved towards each other so as to avoid excessive clamping which would lead to the points being splayed apart. This abutment is situated level with the centering means 8a, 8b, 9a, 9b.

In the embodiment of FIGS. 1 and 2, the handle is shorter than the tweezers, i.e. the working part 1 is longer than the elements 4 and 5. These elements are carried by the branches of the tweezers 1, and the tweezers possess a root portion 1a of the branches, which root portion is of a length that is practically the same as the length of the branches. By selecting an appropriate length for the root portion 1a of the part 1, it is possible to compensate for the forward unbalance due to the weight of the handle.

The way in which the elements 4 and 5 are fastened on the branches 2 and 3 depends on the nature of the materials to be assembled together. When both materials are metals, fastening can be performed by laser welding as represented by points A and B in FIG. 1. In other circumstances, fastening is provided by adhesive, or ultrasound bonding, . . . .

The embodiment of the tweezers shown in the following FIGS. 3 to 5 has a working part 10 of a design that is different from that of the above-described part 1. The two branches 12 and 13 of this part extend from a root portion 11 that is much shorter than the above root portion. The free end 12a, 13a of each branch is provided with a point that is hook-shaped, extending away from the plane P in which the branches move. The connections between the root portion 11 and the branches 12 and 13 takes place via zones 11a and 11b of a width l that is defined by machining and that determines the resilient stiffness of the tweezers. Thus, starting from a given blank, it is possible to fabricate tweezers having different qualities for different applications in order to satisfy all the requirements of surgeons.

Each branch possesses a projecting portion 12b, 13b limiting the clamping movement of the tweezers, these projections being of complementary shapes (a tip for the projection 13b and a V-shape for the projection 12b). In the vicinity of this abutment, each branch carries an outwardly-directed tab 12c, 13c constituting a tooth that is inclined towards the point.

In FIG. 4, the part 10 is shown mounted in a handle that has two elements 14 and 15. FIG. 5 is a plan view looking along arrow F of FIG. 4, showing the element 15.

Each of the elements 14 and 15 is of elongate shape to present a convex outside surface 14a, 15a, and a substantially plane inside surface 14b, 15b with a respective groove 16, 17, like the tweezers described above. The bottom of each groove has an opening 16a, 17a for receiving the outer inclined tooth 12c, 13c of each branch 12, 13 of the working part 10. The openings 16a, 17a are likewise forwardly inclined, i.e. the distal end of each opening forms a tooth 16b, 17b complementary to the corresponding tooth 12c, 13c of the working part when the working part is received in the groove 16, 17.

The other end 16c, 17c (proximal end) of the groove 16, 17 is suitable for preventing the handle element from moving longitudinally on the working part by co-operating with the corresponding tooth. For this purpose, the length of the groove, i.e. the dimension between the opening 16a, 17a and the corresponding end 16c, 17c lies within tolerances that ensure, once the part 10 is received in each of the grooves, that it cannot escape therefrom merely by sliding longitudinally relative to the handle.

At its end near to the points of the tweezers, each of the elements 14, 15 of the handle is provided with centering means 18b, 19a, 19b similar to those described above. The other end of each handle element is shaped to form a flat tail 20, 21 substantially perpendicular to the plane P of the working part 10 (and in which it moves), the tail 20 being provided with pressure snap-fastener means 22 that co-operate with complementary means provided at the tail 21 of the other handle element. These snap-fastener means are represented only symbolically, since they may take numerous appropriate forms that are known in themselves (permanent snap-fastening with serrations, or releasable snap-fastening with press buttons, . . . ). This variant embodiment makes it possible to fabricate handles in a standardized manner suitable for receiving a plurality of types of working part. In addition, if the snap-fastening is releasable, the tweezers of the invention are easily recycled.

With reference more particularly to FIG. 5, it can be seen that a groove such as 17 has zones 17e, 17f of calibrated width and of short extent so as to enable said width to be accurately controlled by an injection fabrication method. This width corresponds to the width e of the plate from which the blank for the working part is derived. It will be understood that just two precise zones suffice to determine said dimension e of the working part and that as a result, if the initial plate is of thickness that is too variable, a single surfacing pass is required only locally, on regions of the plate that are to be received in these zones of calibrated width.

Figure 6:
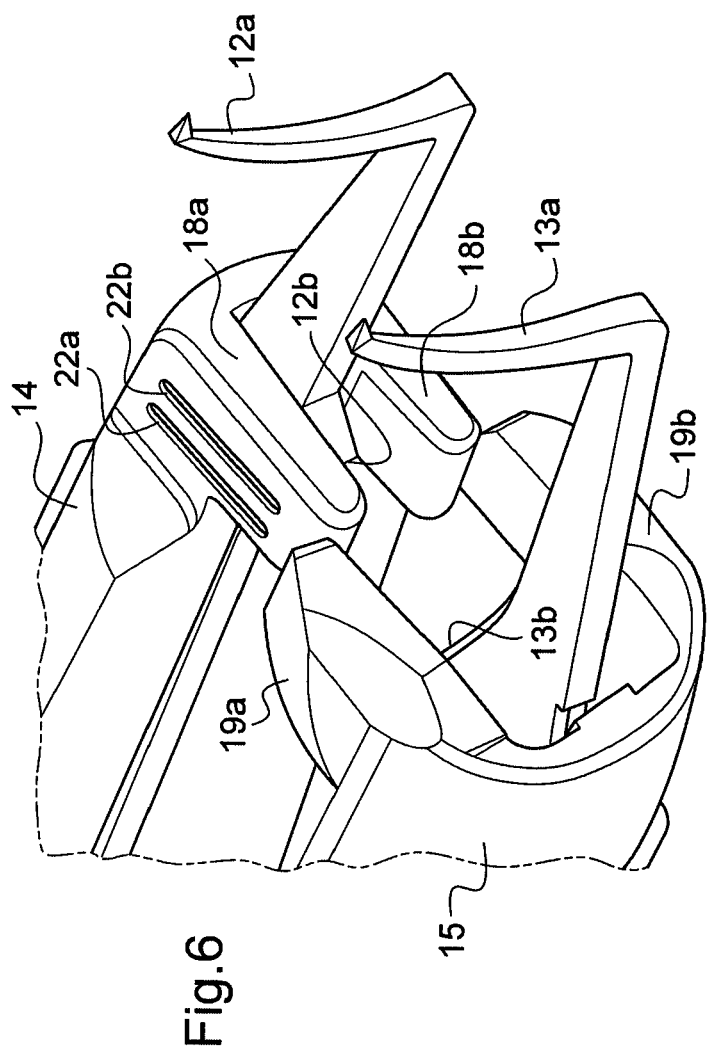
FIG. 6 shows the end of a variant embodiment of tweezers as shown in FIGS. 4 and 5.

FIG. 6 is a perspective view of an end of a variant embodiment of the tweezers shown in FIGS. 3 and 4.

In this figure, there can be seen the same elements as described above with the same references.

Thus, at the ends of the handle elements 14 and 15 that are close to the points 12a and 13a of the tweezers, there can be seen the centering means 18a, 18b and 19a, 19b. More precisely, the fins 19a and 19b provided at the end of the body 15 are disposed so as to lie outside the projecting portions 18a and 18b of the element 14 facing the fins. The projections 18a, 18b guide the diverging fins in wedge-like manner when they take up positions on either side thereof, while the tweezers are being closed by the fingers of the operator. Their outside faces converge towards the opposite branch of the tweezers while the inside faces of the fins 19a, 19b diverge going towards the opposite branch. Centering is achieved by the outside and inside faces coming into coincidence. It is possible in some circumstances for centering not to occur before the points make contact, given the dimensional uncertainties involved in fabricating elements out of plastics material, and those that result from mounting the elements 14 and 15 on the working part of the tweezers. That constitutes a drawback since on each occasion that the tweezers are closed, making the points coincide become more chancy. The force applied by the surgeon on the handle of the tweezers can induce small torque forces that tend to create twisting in the metal part forming the active portion of the tweezers with the ends 12a, 13a shifting relative to each other in a manner that is not completely countered by the centering means.

In the variant shown, in order to remedy that drawback, a disposition is provided that substantially guarantees contact and thus centering between the elements 18a, 18b and the elements 19a, 19b of the other branch.

This disposition consists in two portions in relief 22a, 22b provided on the outside face of at least one and preferably both projections 18a, 18b. These portions in relief are made integrally with the material of the handle 14 and they are of a size such that firstly they come into contact with the inside faces of the fins 19a and 19b prior to complete closure of the tweezers, and secondly, when closure continues after contact has been made, these portions in relief are flattened by plastic deformation. These flattened portions in relief then become the contact surfaces and they thus serve to center the branches of the tweezers relative to each other in a manner that is shaped exactly to obtain perfect coincidence between the points of the tweezers 12a, 13a, providing that the operator takes care on first closure to ensure that they come into such coincidence.

Naturally, these portions in relief may be made on the inside faces of the fins 19a, 19b, or they may be shared between the surfaces for guiding closure of the tweezers.

Reference is made finally to FIG. 7, which shows portions in relief 23a and 23b that are also designed to be flattened at least in part when the metal active portion 10 of the tweezers is received in the groove 14 of each handle element 14 or 15. This ensures that the housing of said portion does not "float" laterally in the handle elements. These portions in relief are preferably situated in the zones 17c and 17f of the slots, zones where the transverse size thereof is best controlled.

What is claimed is:

1. Tweezers for microsurgery, in particular ophthalmological surgery, the tweezers comprising a one-piece working part (1, 10) of U-shape, with the free ends (2a, 3a, 12a, 13a) of each branch (2, 3, 12, 13) being shaped into a point, the part being derived from a flat blank of thickness (e) constituting the dimension perpendicular to the plane (P) in which the branches (2, 3, 12, 13) move, and elements for manipulating the working part together forming a handle for gripping the tweezers, wherein each element is in the form of an elongate body (4, 5, 14, 15) presenting a convex outside surface (4a, 5a, 14a, 15a) and a substantially planar surface (4b, 5b, 14b, 15b) having a longitudinal groove (6, 7, 16, 17) hollowed out therein to house one of the branches (2, 3, 12, 13) of the working part (1, 10), the end of each handle element facing towards the free ends being provided with centering means (8a, 8b, 9a, 9b, 18b, 19a, 19b) cooperating with a complementary centering member of the corresponding end of the other element;

- wherein the centering means are constituted at least by fins (8a, 8b, 9a, 9b, 18b, 19a, 19b) provided on one of the bodies (4, 5, 14, 15) and projecting towards the other body beyond the planar surface (4b, 5b, 14b, 15b) having the groove (6, 7, 16, 17) so as to fit closely on either side of a complementary portion (8a, 8b, 9a, 9b, 18b, 19a, 19b) at the end of the other body during closure of the tweezers;
- wherein the fins (9a, 9b, 19a, 19b) advantageously diverge away from the planar surface while the complementary portion (8a, 8b, 18b) presents the shape of a wedge having two slopes that becomes progressively received between the fins during the closure movement of the tweezers; and
- wherein the two handle elements (4, 5) of the tweezers are of length shorter than the total length of the working part (1), each then being fitted on the corresponding branch (2, 3) by the branch being engaged in the groove (6, 7) and by fastening by any means appropriate for the materials constituting the working part and the handle.

2. Tweezers according to claim 1, wherein each branch (2, 3, 12, 13) is provided, facing the other branch, with a projection (2b, 3b, 12b, 13b) constituting an abutment for stopping closure, said abutment being situated level with the above-mentioned centering means.

3. Tweezers according to claim 1, wherein the working part (1) possesses a root portion of the branches (2, 3) extending well beyond the rear ends (proximal ends) of the handle elements (4, 5) so as to facilitate handling of the tweezers by the operator.

4. Tweezers according to claim 1, wherein the handle elements (14, 15) are of injected plastics material, and in that each element includes a groove (16, 17) with a bottom that includes an opening (16a, 17a) for receiving an inclined connection tooth (12c, 13c) on the outside of a branch (12, 13) of the tweezers, the proximal end (16c, 17c) of the groove being suitable, in co-operation with the tooth, for preventing the handle element (14, 15) moving on the working part (10), while the end of said handle element is shaped as a flat tail (20, 21) substantially perpendicular to the plane (P) of the working part in service, said tail being provided with pressure-operated snap-fastener means (22) co-operating with complementary means provided on the tail of the other handle element.

5. Tweezers according to claim 4, wherein at least one or the other of the fins (19a, 19b) or of the complementary portions (18a, 18b) includes portions in relief (22a, 22b) on at least one of its active faces such that on the first occasion the branches of the tweezers are moved towards each other, the portions in relief (22a, 22b) are flattened, at least in part, by plastic deformation.

6. Tweezers according to claim 4, wherein one of the flanks of each groove (17) is provided with at least one portion in relief (23a, 23b) that is suitable for being deformed plastically by inserting the working part (10) in the groove.

7. Tweezers according to claim 1, wherein the zones (11a, 11b) connecting the root portion (11) of the branches to the branches (12, 13) of the working part are of controlled width l.

* * * * *